United States Patent
Albrecht et al.

(10) Patent No.: US 9,440,971 B2
(45) Date of Patent: Sep. 13, 2016

(54) SOLID STATE FORMS OF VEMURAFENIB HYDROCHLORIDE

(71) Applicant: ratiopharm GmbH, Ulm (DE)

(72) Inventors: Wolfgang Albrecht, Ulm (DE); Richard Guserle, Kotz (DE); Frank Lehmann, Ulm (DE)

(73) Assignee: ratiopharm GmbH, Ulm (DE)

( * ) Notice: Subject to any disclaimer, the term of this patent is extended or adjusted under 35 U.S.C. 154(b) by 0 days.

(21) Appl. No.: 14/772,566

(22) PCT Filed: Mar. 11, 2014

(86) PCT No.: PCT/US2014/023166
§ 371 (c)(1),
(2) Date: Sep. 3, 2015

(87) PCT Pub. No.: WO2014/159353
PCT Pub. Date: Oct. 2, 2014

(65) Prior Publication Data
US 2016/0016950 A1    Jan. 21, 2016

Related U.S. Application Data

(60) Provisional application No. 61/783,651, filed on Mar. 14, 2013.

(51) Int. Cl.
*C07D 401/02* (2006.01)
*C07D 401/10* (2006.01)
*A61K 31/4353* (2006.01)
*A61K 31/437* (2006.01)
*C07D 471/04* (2006.01)

(52) U.S. Cl.
CPC .................................. *C07D 471/04* (2013.01)

(58) Field of Classification Search
CPC .............. C07D 401/02; C07D 401/10; A61K 31/4353
USPC .......................................... 546/121; 514/300
See application file for complete search history.

(56) References Cited

U.S. PATENT DOCUMENTS 7,863,288 B2    1/2011  Ibrahim et al.
8,865,735 B2 *  10/2014 Ibrahim ............... A61K 31/437
                                                           514/300

FOREIGN PATENT DOCUMENTS

| WO | WO 2010/114928 | 10/2010 |
| WO | WO 2010/129570 | 11/2010 |
| WO | WO 2012/161776 | 11/2012 |
| WO | WO 2014/008270 | 1/2014 |

OTHER PUBLICATIONS

Bastin et al., "Salt Selection and Optimisation for Pharmaceutical New Chemical Entities", Organic Process Research and Development, vol. 4, No. 5, pp. 427-435, 2000.

Morissette et al., "High-Throughput Crystallizations: Polymorphs, Salts, Co-Crystals and Solvates of Pharmaceutical Solids", Advanced Drug Delivery Reviews, Elsevier, Amsterdam, Nl, vol. 56, No. 3, pp. 275-300, 2004.

* cited by examiner

*Primary Examiner* — Niloofar Rahmani
(74) *Attorney, Agent, or Firm* — Baker & Hostetler LLP

(57) ABSTRACT

Provided herein are solid state forms of Vemurafenib hydrochloride, processes for preparing the solid state forms, as well as pharmaceutical compositions and formulations comprising said solid state forms.

6 Claims, 3 Drawing Sheets

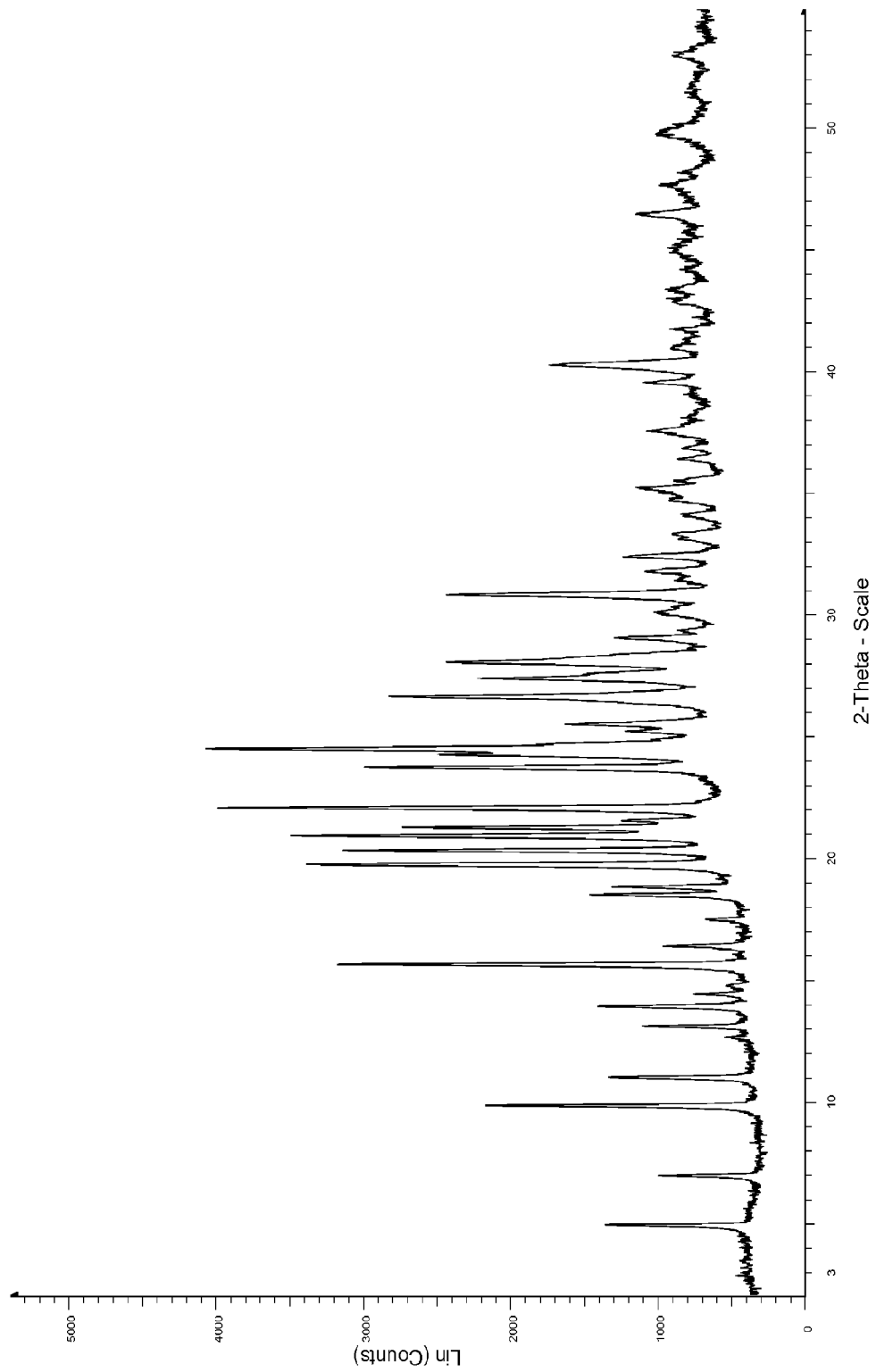
Figure 1: A powder X-ray diffraction pattern for crystalline Vemurafenib hydrochloride Form II

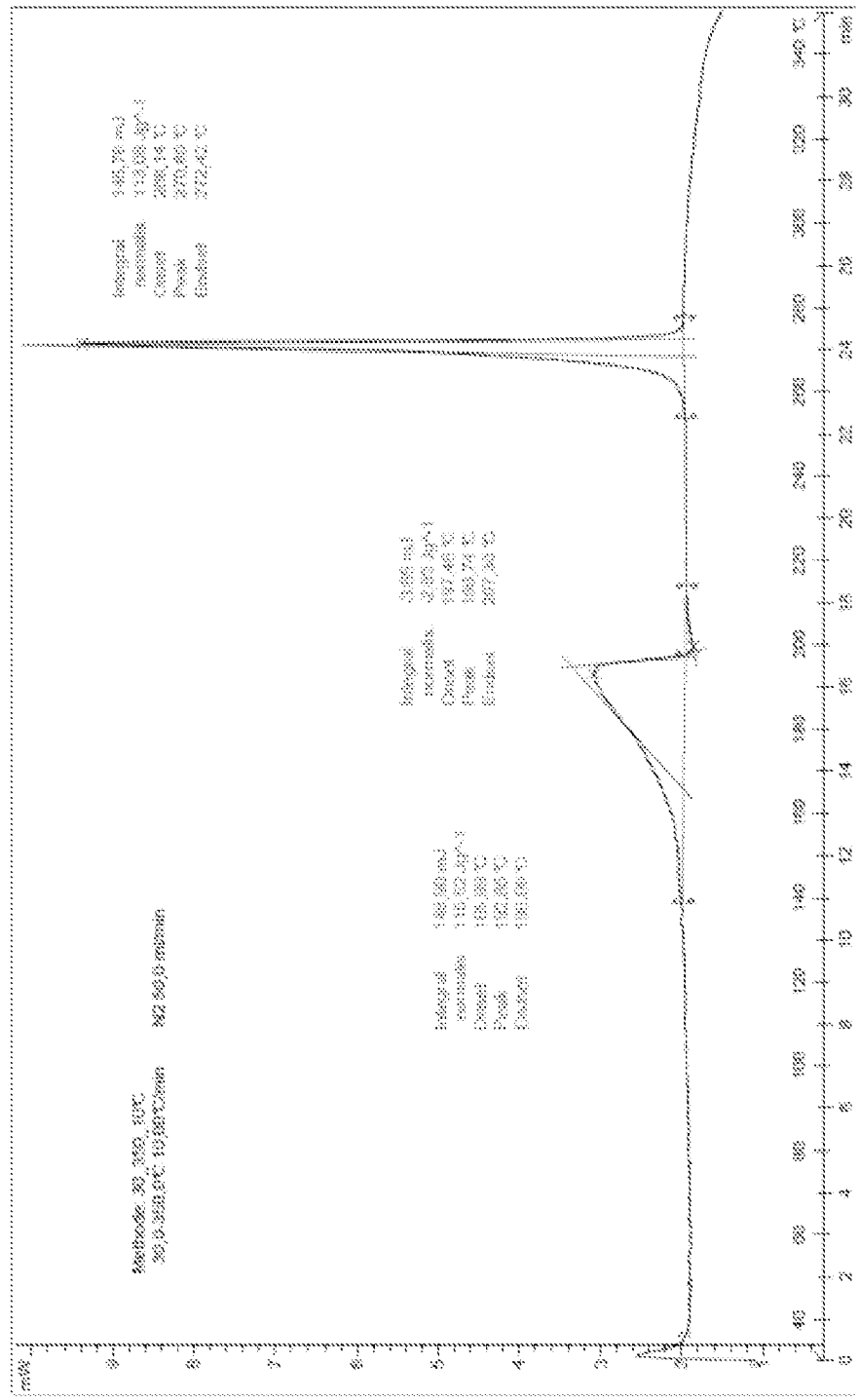
Figure 2: A DSC thermogram of Vemurafenib hydrochloride, Form II.

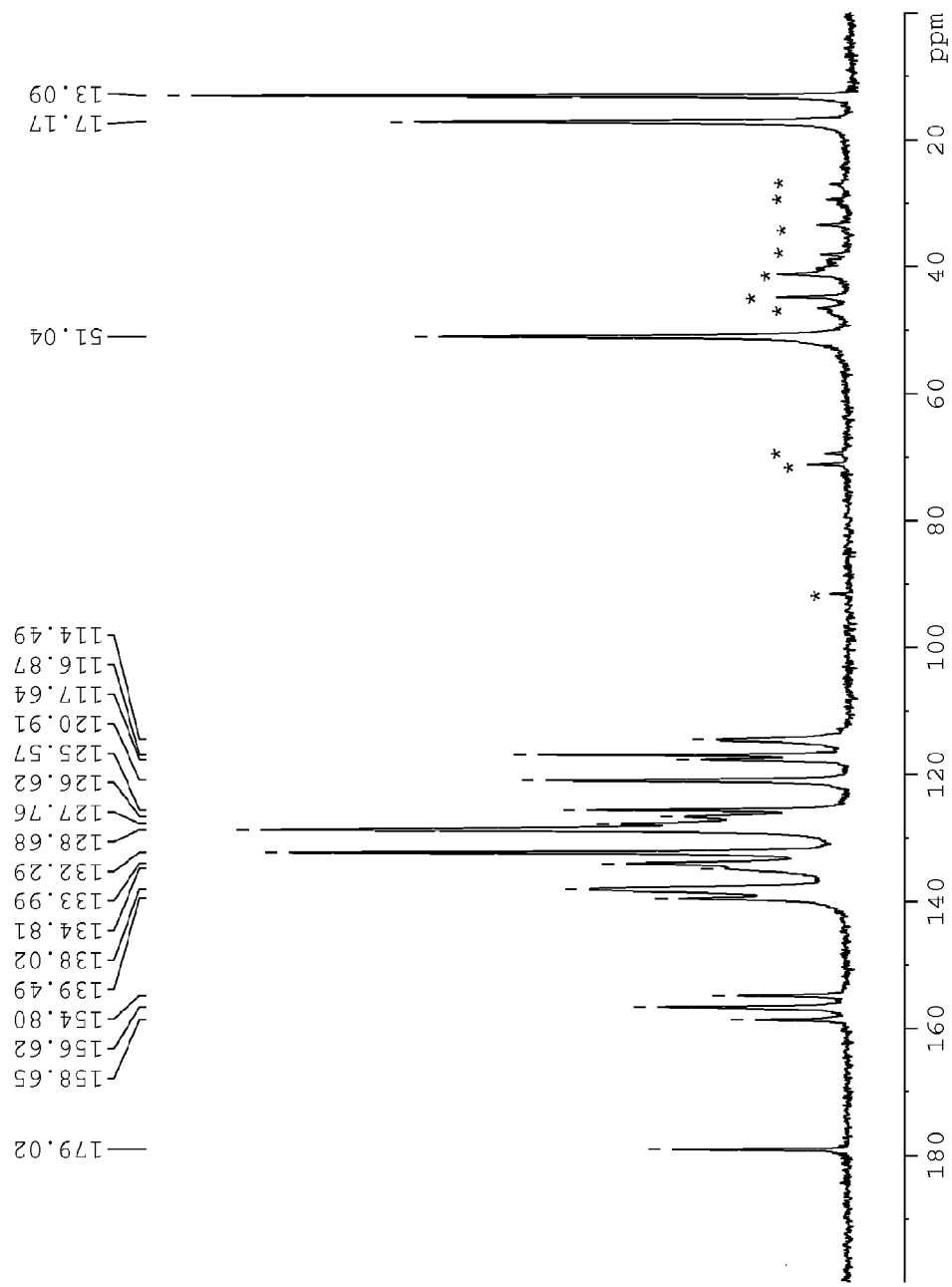
Figure 3: A solid state 13C NMR spectrum of Vemurafenib hydrochloride, Form II.

SOLID STATE FORMS OF VEMURAFENIB HYDROCHLORIDE

CROSS-REFERENCE TO RELATED APPLICATIONS

This application is the National Stage of International Application No. PCT/US2014/023166, filed Mar. 11, 2014, which claims the benefit of U.S. application No. 61/783,651, filed Mar. 14, 2013, the disclosures of which are incorporated herein by reference in their entireties.

FIELD OF THE INVENTION

The present invention relates to a solid state form of Vemurafenib hydrochloride, processes for the preparation thereof, formulations comprising thereof, and the conversion of the solid state form to Vemurafenib base and/or other Vemurafenib salts.

BACKGROUND OF THE INVENTION

Vemurafenib, propane-1-sulfonic acid {3-[5-(4-chlorophenyl)-1H-pyrrolo[2,3-b]pyridine-3-carbonyl]-2,4-difluoro-phenyl}-amide, has the following chemical structure:

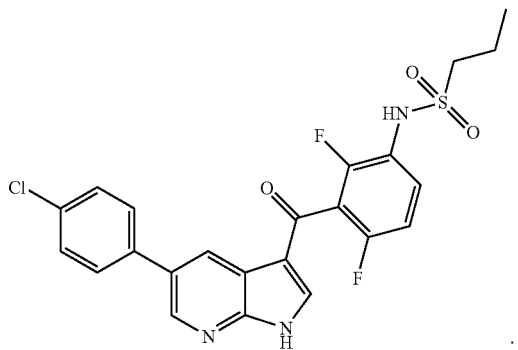 [SMILES: CCCS(=O)(=O)Nc1ccc(F)c(C(=O)c2c[nH]c3ncc(-c4ccc(Cl)cc4)cc23)c1F]

Vemurafenib is a BRAF kinase inhibitor, which is marketed under the trade name ZELBORAF® for the treatment of patients with metastatic melanoma with the BRAF V600E mutation.

Vemurafenib is disclosed in U.S. Pat. No. 7,863,288. WO 2010/114928 discloses forms 1 and 2 of Vemurafenib, and discloses the mesylate, tosylate, maleate, oxalate, and dichloroacetate salts. WO 2010/129570 discloses non-crystalline complexes of Vemurafenib and its L-arginine and L-lysine salts. WO 2014/008270 discloses choline and esylate salts of Vemurafenib; and WO 2012/161776 discloses additional solid forms and salts of Vemurafenib, including the hydrochloride salt and a crystalline form thereof.

Polymorphism, the occurrence of different crystal forms, is a property of some molecules and molecular complexes. A single molecule, like Vemurafenib or salts thereof, may give rise to a variety of polymorphs having distinct crystal structures and physical properties like melting point, thermal behaviors (e.g. measured by thermogravimetric analysis—"TGA", or differential scanning calorimetry—"DSC"), powder X-ray diffraction (PXRD) pattern, infrared absorption fingerprint, and solid state NMR spectrum. One or more of these techniques may be used to characterize a particular polymorph and to distinguish different polymorphic forms of a compound.

Different solid state forms (including solvated forms) of an active pharmaceutical ingredient may possess different properties. Such variations in the properties of different solid state forms and solvates may provide a basis for improving certain aspects of the API, such as its formulation, for example, by facilitating better processing or handling characteristics, changing the dissolution profile in a favorable direction, or improving stability (polymorph as well as chemical stability) and shelf-life. These variations in the properties of different solid state forms may also offer improvements to the final dosage form, for instance, if they serve to improve bioavailability. Different solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new polymorphic forms and solvates of a pharmaceutical product can provide materials having, inter alia, desirable processing properties, such as ease of handling, ease of processing, chemical and polymorphic stability upon storage and processing, and ease of purification or are useful as advantageous intermediate crystal forms that facilitate conversion to other solid state forms (including other solvates) of said pharmaceutical product.

New polymorphic forms and solvates of a pharmaceutically useful compound can also provide an opportunity to improve the performance characteristics of a pharmaceutical product. It enlarges the repertoire of materials that a formulation scientist has available for formulation optimization, for example by providing a product with different properties, e.g., better processing or handling characteristics, improved dissolution profile, or improved shelf-life. Lastly, new polymorphic forms may be prepared with improved reliability and reproducibility compared to other forms, for example, in terms of crystallinity or polymorphic purity.

SUMMARY OF THE INVENTION

The present invention provides a solid state form of Vemurafenib hydrochloride, processes for the preparation thereof, and pharmaceutical compositions and formulations comprising the solid state form of Vemurafenib hydrochloride, and processes for the preparation of the pharmaceutical compositions and formulations.

The present invention also provides the use of said solid state form of Vemurafenib hydrochloride for the manufacture of pharmaceutical compositions and formulations. Accordingly, the present invention further provides a pharmaceutical composition comprising said solid state form of Vemurafenib hydrochloride of the present invention. The pharmaceutical composition may additionally comprise at least one pharmaceutically acceptable excipient to form a pharmaceutical formulation that can, for example, be administered to patients in need of such treatment.

The present invention comprises a process for preparing the above-mentioned pharmaceutical formulations. The process comprises combining the solid state form of Vemurafenib hydrochloride with at least one pharmaceutically acceptable excipient.

The solid state form as defined herein as well as the pharmaceutical compositions and formulations of Vemurafenib hydrochloride can be used as medicaments, particularly for the treatment of cancer. The present invention also provides a method of treating cancer comprising administering a therapeutically effective amount of the solid state form of Vemurafenib hydrochloride of the present invention, or a therapeutically effective amount of at least one of the pharmaceutical compositions or formulations of the present invention comprising said solid state form of Vemurafenib hydrochloride of the present invention to a patient in need thereof.

The present invention also provides the use of said solid state form of Vemurafenib and/or Vemurafenib salt, particularly Vemurafenib hydrochloride, or at least one of the above pharmaceutical compositions and/or formulations for the manufacture of a medicament for treating cancer.

BRIEF DESCRIPTION OF THE FIGURES

FIG. 1 shows a powder X-ray diffraction pattern ("Powder XRD" or "PXRD") for crystalline Vemurafenib hydrochloride form II.

FIG. 2 shows a Differential Scanning Calorimetry ("DSC") thermogram for crystalline Vemurafenib hydrochloride form II.

FIG. 3 shows a solid state $^{13}$C NMR spectrum for crystalline Vemurafenib hydrochloride form II.

DETAILED DESCRIPTION OF THE INVENTION

The present invention provides a solid state form of Vemurafenib hydrochloride, processes for preparing the solid state form, as well as pharmaceutical compositions and formulations comprising said solid state form.

In accordance with WO 2010/114928 and WO 2010/129570, it was observed that Vemurafenib has an extremely low solubility which makes it difficult to formulate and may result in poor bioavailability.

Amorphous Vemurafenib may improve solubility, however it is not stable. WO 2010/129570 also states that other base-addition salts, such as the sodium and potassium salts are difficult to isolate and hygroscopic. In addition, it was found that those salts also contain large amounts of residual solvent. Attempts to develop stable, solvent-free and robust crystalline form of such salts were not successful. The Vemurafenib arginine and lysine complexes described in WO 2010/129570 are stated to be non-crystalline complexes. However, their PXRD pattern shows some degree of crystallinity.

Consistent with the latter, it was found that the conversion of Vemurafinib free base to acid addition or base addition salts was in many cases not possible, rather leading to precipitation of the free base, or yielding non-crystalline complexes of the free base and the respective acid or base. For example, it was observed that a conversion into a variety of amine salts of vemurafenib could not be accomplished.

The present invention offers crystalline Vemurafenib HCl, which can be in anhydrous form. The highly crystalline Vemurafenib HCl of the present invention has good solubility and high chemical and crystalline purities which makes it suitable as a pharmaceutically acceptable salt. The crystalline Vemurafenib HCl of the present invention can be directly used to prepare highly soluble formulations, without the need of a solid dispersion formulation comprising the active ingredient in amorphous form. The latter is less economical and burdened with potential re-crystallization of the active ingredient, making quality control of solid dispersions more demanding as even a partial re-crystallization, which may have a substantial impact on dissolution properties of the drug substance and thus clinical efficacy, must be controlled.

Depending on which other solid state form it is compared with, the solid state form of the present invention may have advantageous properties selected from at least one of: chemical or polymorphic purity, increased crystallinity, flowability, solubility, dissolution rate, bioavailability, morphology or crystal habit, specific surface and pycnometric density, bulk/tap density, stability—such as chemical stability as well as thermal and mechanical stability with respect to polymorphic conversion, stability towards dehydration and/or storage stability, a lower degree of hygroscopicity, low content of residual solvents and advantageous processing and handling characteristics such as compressibility, and bulk density.

Solid state forms of Vemurafenib hydrochloride comprise crystal forms, or crystalline forms, of Vemurafenib hydrochloride. As used herein, solid state forms, crystal forms, crystalline forms, polymorphs and polymorphic forms are used interchangeably.

A crystal form may be referred to herein as being characterized by graphical data "substantially as depicted in" a Figure. Such data include, for example, powder X-ray diffractograms and solid state NMR spectra. The graphical data potentially provides additional technical information to further define the respective solid state form which can not necessarily or easily be described by reference to numerical values for peak positions and/or relative intensities. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms.

As used herein, the expression "chemical shift difference" refers to the difference in chemical shifts between a reference signal and another signal in the same NMR spectrum. These chemical shift differences serve to provide an additional analytical measurement for a substance, for example a Vemurafenib hydrochloride crystal form of the present invention, which will compensate for a phenomenon that may occur in NMR spectroscopy wherein a shift in the solid-state NMR "fingerprint" is observed. Such a shift in the NMR peaks may occur, for example, as a result of variations in the instrumentation, the temperature, or the calibration method used in the NMR analysis. This shift in the solid-state NMR "fingerprint", having chemical shift resonances at a certain positions, is such that even though the individual chemical shifts of signals have moved, all the peaks in the spectrum are moved be the same amount, such that the difference between chemical shifts of each signal and another is retained. Thus, this shift may be used as a reliable characterization of the material being analyzed.

In the present patent application the chemical shift differences were calculated by subtracting the chemical shift value of the signal exhibiting the lowest chemical shift (reference signal) in the solid state $^{13}$C NMR spectrum in the range of 0 to 180 ppm from the chemical shift value of another (observed) signal in the same $^{13}$CNMR spectrum in the range of 100 to 180 ppm.

A crystal form (or polymorph) may be referred to herein as substantially free of any other crystalline (or polymorphic) forms. As used herein in this context, the expression "substantially free of any other forms" will be understood to mean that the crystalline form contains 20% or less, 10% or less, 5% or less, 2% or less, or 1% or less of any other forms of the subject compound as measured, for example, by PXRD. Thus, polymorphs of Vemurafenib hydrochloride described herein as substantially free of any other polymorphic forms would be understood to contain greater than 80% (w/w), greater than 90% (w/w), greater than 95% (w/w), greater than 98% (w/w), or greater than 99% (w/w) of the subject polymorphic form of Vemurafenib hydrochloride. Accordingly, in some embodiments of the invention, the described polymorphs of Vemurafenib hydrochloride may contain from 1% to 20% (w/w), from 5% to 20% (w/w), or from 5% to 10% (w/w) of one or more other crystal forms of Vemurafenib or salts thereof.

The amount of solvent employed in a chemical process, e.g., a reaction or a crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding MTBE (1.5 v/v) to a 100 ml reaction mixture would indicate that 150 mL of MTBE was added.

As used herein, the expression "room temperature" or "RT" refers to a temperature between about 20° C. and about 30° C. Usually, room temperature ranges from about 20° C. to about 25° C.

As used herein, the term "overnight" refers to a period of between about 15 and about 20 hours, typically between about 16 to about 20 hours.

As used herein, the term "reduced pressure" refers to a pressure of about 10 mbar to about 50 mbar.

As used herein, the term "isolated" corresponds to product or solid state form thereof that is physically separated from the reaction mixture in which it is formed.

As used herein, unless stated otherwise, XRPD peaks reported herein are preferably measured using CuK radiation, λ=1.5418.

As used herein, the expression "wet crystalline form" refers to a polymorph that was not dried using any conventional techniques to remove residual solvent. Such conventional techniques include, but are not limited to, evaporation, vacuum drying, oven drying, drying under nitrogen flow, etc.

As used herein, the expression "dry crystalline form" refers to a polymorph that was dried using any conventional techniques to remove residual solvent. Such conventional techniques include, but are not limited to, evaporation, vacuum drying, oven drying, drying under nitrogen flow, etc.

As used herein, and unless stated otherwise, the term "anhydrous" in relation to crystalline Vemurafenib hydrochloride relates to a crystalline Vemurafenib hydrochloride which contains no more than 1% (w/w) of either water or organic solvents as measured by conventional methods, for example TGA, GC or KF. An anhydrous form of the solid states of Vemurafenib hydrochloride of the present invention refers to a form that does not contain crystalline water (or other solvents) in a defined, stoichiometric amount within the crystal.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, and unless indicated otherwise, the term "polymorphic stability" in relation to the crystalline forms of Vemurafenib hydrochloride means that there is less than 20%, 10%, 5%, 1%, 0.5% or 0.1% conversion of crystalline Vemurafenib hydrochloride to any other solid state form of Vemurafenib hydrochloride under the specified conditions, as measured by PXRD. In some embodiments, the conversion is 0.5%-20%, 0.5%-10% or 0.5%-5% or 0.5%-1% or 0.1%-1%, or 0.1%-0.5%.

As used herein, and unless stated otherwise, the terms "crystalline Vemurafenib form 2", or "form 2 of Vemurafenib" refers to crystalline Vemurafenib as described in WO 2010/114928, characterized by an X-ray powder diffraction pattern comprising characteristic peaks at approximately 8.8, 9.2, 13.5, 19.1 and 24.4 degrees 2Theta, or having characteristic peak locations of approximately 6.7, 8.8, 9.2, 13.5, 15.0, 17.7, 19.1, 19.7, 21.4 and 24.4 degrees 2Theta, or having characteristic peak locations of approximately 6.7, 8.8, 9.2, 13.5, 14.1, 14.5, 15.0, 16.2, 17.0, 17.7, 19.1, 19.7, 21.4, 22.2, 24.1, 24.4, and 28.1 degrees 2Theta.

As used herein, and unless stated otherwise, the terms "crystalline Vemurafenib hydrochloride form I", or "form I of Vemurafenib hydrochloride" refers to crystalline Vemurafenib hydrochloride as described in WO 2012/161776, characterized by an X-ray powder diffraction pattern comprising characteristic peaks at approximately 6.6, 7.8, 11.2, 12.6, 14.1, 14.7, 16.3, 17.8, 19.3, 19.6, 20.7, 21.5, 22.7, 24.1, 25.4 and 25.8 degrees 2Theta (±0.2 degrees 2Theta).

The present invention encompasses a crystalline form of Vemurafenib hydrochloride, designated as Form II.

Form II of Vemurafenib hydrochloride can be characterized by data selected from one or more of the following: a powder X-ray diffraction pattern having peaks at 5.0, 9.9, 15.7, 19.8 and 22.1 degrees two theta±0.2 degrees two theta; a powder X-ray diffraction pattern substantially as depicted in FIG. 1; a solid-state $^{13}$C NMR spectrum having characteristic peaks at 51.0, 114.5, 132.3, 138.0 and 139.5 ppm, ±0.2 ppm; a solid state $^{13}$C NMR spectrum having chemical shift differences between said characteristic peaks and a peak at 120.9 ppm±0.2 ppm of −69.9, −6.4, 11.4, 17.1 and 18.6±0.1 ppm, respectively; a solid state $^{13}$C NMR spectrum substantially as shown in FIG. 3; and any combinations of these data.

Typically, the signal exhibiting the lowest chemical shift in the chemical shift area of 0-200 ppm for form II of Vemurafenib HCl is at 13.1±1ppm.

Form II, characterized by a powder X-ray diffraction pattern having peaks at 5.0, 9.9, 15.7, 19.8 and 22.1 degrees two theta±0.2 degrees two theta, can be further characterized by an additional one, two, three, four or five PXRD peaks selected from 18.5, 20.4, 21.0, 23.8 and 26.7 degrees two theta±0.2 degrees two theta.

Form II can be further characterized by one or more of the following: a DSC thermogram substantially as depicted in FIG. 2; a broad dehydrochlorination endotherm between 166° C. (±5° C.) and 197° C. (±5° C.), a DSC melting peak at about 270.8° C. (±1° C.), and a DSC melting onset at about 268.1° C. (±1° C.); and by any combinations of these data.

Form II can be characterized by any combinations of the above data. For example, by a powder X-ray diffraction pattern having peaks at 5.0, 9.9, 15.7, 19.8 and 22.1 degrees two theta±0.2 degrees two theta and also by a DSC thermogram substantially as depicted in FIG. 2.

In certain embodiments, form II is an anhydrous form, as can be determined, for example, by TGA.

The above form II of Vemurafenib HCl has advantageous properties selected from at least one of: chemical or polymorphic purity, flowability, solubility, dissolution rate, bioavailability, morphology or crystal habit, stability—such as such as chemical stability as well as thermal and mechanical stability with respect to polymorphic conversion, storage stability, stability to dehydration, low hygroscopicity, and low content of residual solvents and advantageous processing and handling characteristics such as compressibility, or bulk density.

Particularly, crystalline Vemurafenib HCl form II has high chemical purity and excellent stability properties. Specifically, it is stable upon storage at 25° C. and 60% relative humidity (RH); and at 30° C./65% RH for up to at least 24 weeks; while crystalline Vemurafenib HCl form I converts to Vemurafenib free base under these conditions. Furthermore, crystalline Vemurafenib HCl form II has good solubility and it can be used to prepare an oral formulation, i.e. a tablet or a capsule, without the need of a solid dispersion formulation, or co-precipitation with a polymer. Therefore, the crystalline Vemurafenib HCl form II may be used to prepare an oral formulation which is stable and has a relatively small tablet or capsule size as the molar ratio of Vemurafenib to HCl is about 1:1, which is highly advantageous for preparing pharmaceutical compositions with high drug load.

The described solid state form II of Vemurafenib hydrochloride can be used to prepare Vemurafenib base or other different salts of Vemurafenib, as well as solid state forms thereof and/or pharmaceutical formulations comprising one or more of the salts and/or solid state forms thereof.

The present invention also encompasses a process for preparing other Vemurafenib salts. The process comprises preparing the solid state form II of Vemurafenib hydrochloride for example by the processes of the present invention, and converting that form to said other Vemurafenib salt. The conversion can be done, for example, by a process comprising basifying the above described Vemurafenib hydrochloride solid state form II, and reacting the obtained form with a suitable acid, or a base to obtain the corresponding salt acid addition or base addition salt.

The present invention further encompasses 1) a pharmaceutical composition comprising said solid state form described herein; 2) a pharmaceutical formulation comprising said solid state forms or pharmaceutical compositions described herein, and at least one pharmaceutically acceptable excipient; 3) a process to prepare such formulations comprising combining the above-described solid state forms and at least one pharmaceutically acceptable excipient; 4) the use of the above-described solid state form in the manufacture of a pharmaceutical composition, and 5) a method of treating cancer comprising administering a therapeutically effective amount of the above-described solid state forms, optionally in the form of pharmaceutical compositions or formulations. The present invention also provides a crystalline form of Vemurafenib HCl as described above for use as a medicament, preferably for the treatment of cancer. The pharmaceutical compositions can also be used for preparing said medicament.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

Analytical Methods $^1$H-NMR Spectroscopy

Instrument: Varian Mercury 400 Plus NMR Spectrometer, Oxford AS, 400 MHz.

HPLC/UV

Instrument: HP Series 1090
Column: Discovery C18; 5 m; 150×4.6 mm
Column temp.: Rt
Flow [mL/min]: 1.5
Injection volume: 5 μL
Solvent A: Acetonitrile
Solvent B: 0.01 M $KH_2PO_4$, pH 2.3

|  | time [min] | Solvent B [%] |
|---|---|---|
| Gradient: | 0 | 60 |
|  | 8 | 20 |
|  | 13 | 20 |
|  | 14 | 60 |
|  | 17 | 60 |

Differential Scanning Calorimetry (DSC)
Instrument: Mettler Toledo DSC 822E coupled with a Mettler Toledo Gas-Flow-Controller TS0800GC1 (Mettler-Toledo GmbH, Gießen, Germany)
Aluminium crucible: 40 μL
Lid: Perforated
Temperature range: 30° C. to 350° C.
Heating rate: 10° C./min
Nitrogen flush: 50 mL/min
Software: STARe Version. 8.10
Interpretation: Endothermic modus X-Ray Powder Diffraction (PXRD)
The sample was analyzed on a D8 Advance X-ray powder diffractometer (Bruker-AXS, Karlsruhe, Germany). The sample holder was rotated in a plane parallel to its surface at 20 rpm during the measurement. Further conditions for the measurements are summarized in the table below. The raw data were analyzed with the program EVA (Bruker-AXS, Germany). The samples were layered onto a silicon specimen holder.

|  | standard measurement |
|---|---|
| Radiation | Cu $K_\alpha$ ($\lambda$ = 1.5406 Å) |
| Source | 38 kV/40 mA |
| Detector | Vantec |
| detector slit | variable |
| divergence slit | v6 |
| antiscattering slit | v6 |
| 2θ range/° | 2 ≤ 2θ ≤ 55 |
| step size/° | 0.017 |

Solid State $^{13}$C NMR Spectroscopy Method:
$^{13}$C NMR at 125 MHz using Bruker Avance II+500
SB probe using 4 mm rotors
Magic angle was set using KBr
Homogeneity of magnetic field checked using adamantane
Parameters for Cross polarization optimized using glycine
Spectral reference set according to glycine as external standard (176.03 ppm for low field carboxyl signal, relative to the signal of tetramethylsilane)

Scanning Parameters:
Magic Angle Spinning Rate: 11 kHz
Delay time: 5 s
Number of Scans: 1024
Acquisition time: 30 ms

EXAMPLES

Example 1

Preparation of Vemurafenib Base

Vemurafenib was prepared in four steps according to the procedure described in the following scheme.

Step a: Preparation of Intermediate 4

(propane-1-sulfonic acid {3-[5-(4-chloro-phenyl)-1-(2,6-dichloro-benzoyl)-1H-pyrrolo[2,3-b]pyridine-3-carbonyl]-2,4-difluoro-phenyl}-amide)

Under a stream of nitrogen, 300 g (0.48 mol) intermediate 3 (propane-1-sulfonic acid {3-[5-bromo-1-(2,6-dichloro-benzoyl)-1H-pyrrolo[2,3-b]pyridine-3-carbonyl]-2,4-difluoro-phenyl}-amide) and 81.74 g (0.52 mol, 1.1 eq.) 4-chlorophenylboronic acid were suspended in 1.3 L toluene, instead of anisole as shown in the scheme above. Sodium carbonate (202 g, 1.90 mol, 4 eq.) and water (1.1 L) were added at 25° C. and the mixture was heated to 70° C.

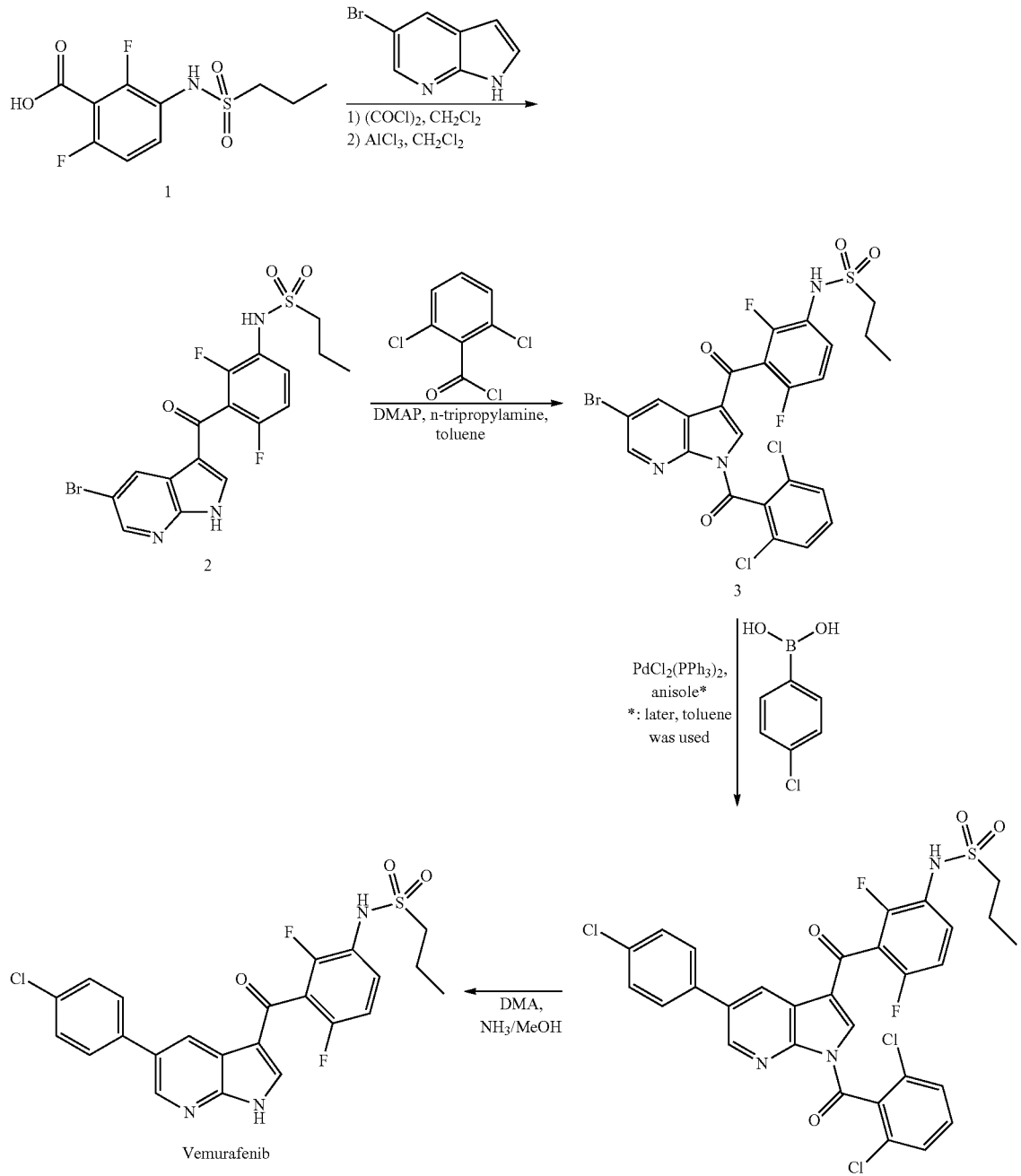

Afterwards, bis(triphenylphosphine)palladium(II) chloride (3.33 g, 4.8 mmol, 0.01 eq.) was added and the reaction mixture was heated to 80-88° C. (external temperature did not exceed 110° C.) for 2 hours. Then the reaction was cooled to 70° C., the two phases were separated and the organic phase was washed at 70° C. with 0.1N $H_2SO_4$ (1.3 L) and water (1.3 L). The organic layer was evaporated to dryness. Propane-1-sulfonic acid {3-[5-(4-chloro-phenyl)-1-(2,6-dichloro-benzoyl)-1H-pyrrolo[2,3-b]pyridine-3-carbonyl]-2,4-difluoro-phenyl}-amide (359.73 g, 114.2%) was isolated as a reddish, glassy solid (yield higher than 100% due to residual toluene).

Step b: Preparation of Vemurafenib

Intermediate 4 (788 g 1.19 mol, propane-1-sulfonic acid {3-[5-(4-chloro-phenyl)-1-(2,6-dichloro-benzoyl)-1H-pyrrolo[2,3-b]pyridine-3-carbonyl]-2,4-difluoro-phenyl}-amide) was suspended at 25° C. in 1200 mL DMF and 900 mL methanol. To this suspension, 700 mL 15% ammonia in methanol (4.77 mol, 4.01 eq.) were added and the mixture was heated to 50-55° C. for 18 hours. The resulting clear solution was concentrated (330 mbar/55° C.), until no ammonia was smelled. Afterwards methanol (4 L) was added slowly over 30 minutes, whereby the temperature was kept between 45-55° C. The resulting suspension was cooled to 25° C. and stored at 4° C. overnight. The solid was filtered, washed with methanol (1 L) and dried under vacuum (50° C./40 mbar). Vemurafenib (374.85 g, 64.4%) was isolated as an off-white solid.

Example 2

Preparation of Vemurafenib-HCl, Form II

Vemurafenib (Form 2, 0.5 g, 1.02 mmol) was suspended in 5 mL acetone and the mixture was warmed to 35° C. While maintaining this temperature, 0.8 ml of 1.25 M HCl in ethanol (approximately 1 equivalent) were added dropwise. A clear solution was obtained. Thereafter, the solution was allowed to cool to RT and stirred overnight. The obtained precipitate was filtered, washed with acetone and dried under ambient conditions (RT, atmospheric pressure) for approximately 20 h. Yield: 0.49 g (91%).

Example 3

Preparation of Vemurafenib-HCl, Form II

The procedure was identical to that described in Example 2 with the following modification: 1.0 ml of 1M HCl in diethylether instead of 0.8 ml of 1.25 M HCl in ethanol, corresponding to 1 equivalent of HCl, was added to the suspension of 0.5 g Vemurafenib in 5 ml acetone. Yield: 0.50 g (93%)

Example 4

Preparation of Vemurafenib-HCl, Form II

Vemurafenib (97.8 g, 199.6 mmol) was suspended in 900 mL acetone and the mixture was warmed to 35° C. While maintaining this temperature, 200 ml of 1.25 M HCl in ethanol (250 mmol HCl, 1.25 equivalents) were added dropwise. A clear solution was obtained. Thereafter, the solution was stirred for another 5 min at 35° C. and then allowed to cool to RT and stirred overnight. The obtained precipitate was filtered, washed with acetone and dried at 40° C. under reduced pressure (30 mbar) for approximately 16 h. Yield: 95.8 g (91%)

What is claimed is:

1. A crystalline form of Vemurafenib hydrochloride salt, designated as Form II, characterized by one or more of the following:
   a powder X-ray diffraction pattern having peaks at 5.0, 9.9, 15.7, 19.8 and 22.1 degrees two theta±0.2 degrees two theta;
   a powder X-ray diffraction pattern substantially as depicted in FIG. 1;
   a solid-state 13C NMR spectrum having characteristic peaks at 51.0, 114.5, 132.3, 138.0 and 139.5 ppm, ±0.2 ppm;
   a solid state 13C NMR spectrum having chemical shift differences between said characteristic peaks and a peak at 120.9 ppm±0.2 ppm of −69.9, −6.4, 11.4, 17.1 and 18.6±0.1 ppm, respectively;
   a solid state 13C NMR spectrum substantially as shown in FIG. 3;
   or any combination of these data.

2. The crystalline form of claim 1, characterized by a powder X-ray diffraction pattern having peaks at 5.0, 9.9, 15.7, 19.8 and 22.1, further characterized by an additional one, two, three, four or five PXRD peaks selected from 18.5, 20.4, 21.0, 23.8 and 26.7 degrees two theta±0.2 degrees two theta.

3. The crystalline form of claim 1, further characterized by one or more of the following:
   a DSC thermogram substantially as depicted in FIG. 2;
   a broad dehydrochlorination DSC endotherm between 166°C. (±5°C.) and 197°C. (±5°C.),
   a DSC melting peak at about 270.8°C. (±1°C.), and DSC melting onset at about 268.1°C. (±1°C.),
   or a combination thereof.

4. The crystalline form of claim 1, wherein the crystalline form is an anhydrous form.

5. A pharmaceutical composition comprising the crystalline form of Vemurafenib hydrochloride according to claim 1.

6. A pharmaceutical formulation comprising
   the crystalline form of Vemurafenib hydrochloride according to claim 1 or a pharmaceutical composition comprising the crystalline form of Vemurafenib hydrochloride according to claim 1,
   and at least one pharmaceutically acceptable excipient.

* * * * *